United States Patent
Dominguez et al.

(10) Patent No.: US 7,654,142 B2
(45) Date of Patent: Feb. 2, 2010

(54) METHOD OF IMAGING USING TOPOLOGIC ENERGY CALCULATION

(75) Inventors: Nicolas Dominguez, Tournefeuille (FR); Benoit Mascaro, Toulouse (FR); Vincent Gibiat, Toulouse (FR)

(73) Assignee: Airbus France, Toulouse (FR)

( * ) Notice: Subject to any disclaimer, the term of this patent is extended or adjusted under 35 U.S.C. 154(b) by 469 days.

(21) Appl. No.: 11/526,625

(22) Filed: Sep. 26, 2006

(65) Prior Publication Data
US 2007/0215823 A1 Sep. 20, 2007

(30) Foreign Application Priority Data
Sep. 28, 2005 (FR) .................................. 05 09896

(51) Int. Cl.
G01N 29/44 (2006.01)
G01N 29/52 (2006.01)

(52) U.S. Cl. .............................. 73/602; 73/625; 73/628; 73/598

(58) Field of Classification Search .................. 73/598, 73/628, 625, 602
See application file for complete search history.

(56) References Cited

U.S. PATENT DOCUMENTS

| | | | | |
|---|---|---|---|---|
| 4,287,769 A | * | 9/1981 | Buckley | 73/627 |
| 5,886,263 A | * | 3/1999 | Nath et al. | 73/579 |
| 2007/0006651 A1 | * | 1/2007 | Kruger et al. | 73/579 |

OTHER PUBLICATIONS

Dominguez N., Gibiat V., Arnaud J.L.: "Flaw Imaging with Ultrasound: The Time Domain Topological Gradient Method"—Review of Quantitative Nondestructive Evaluation, vol. 24, Apr. 9, 2005, pp. 859-866, XP002387991.
Dominguez N. et al.: "Time Domain Topological Gradient and Time Reversal Analogy: An Inverse Method for Ultrasonic Target Detection"—Wave Motion, North-Holland, Amsterdam, NL, vol. 42, No. 1, Jun. 2005, pp. 31-52, XP004844177.
Prada C. et al.: "Decomposition of the Time Reversal Operator: Detection and Selective Focusing on Two Scatterers"—Journal of the Acoustical Society of America, AIP/Acoustical Society of America, Melville, NY, US, vol. 99, No. 4, Part 1, Apr. 1, 1996, pp. 2067-2076, XP000599274.

* cited by examiner

Primary Examiner—Hezron Williams
Assistant Examiner—Nashmiya S Fayyaz
(74) Attorney, Agent, or Firm—Oblon, Spivak, McClelland, Maier & Neustadt, L.L.P.

(57) ABSTRACT

The method for obtaining an image of a part to be inspected includes the steps of determining, by simulation, the ultrasonic field ($s_0$) generated by the propagation of a wave in a flawless reference part; transmitting an ultrasonic wave toward the part to be inspected; measuring the field ($u_m$) returned by the part to be inspected; subtracting from the field ($u_m$) returned by the part to be inspected an ultrasonic field ($u_0$) obtained from a previous corresponding measurement on the reference part; calculating a variable related to the topological energy ($E_T$) in the reference part on the basis of the field ($s_0$) determined by simulation and of the field ($u_m-u_0$) obtained by subtraction; and determining the image of the part to be inspected on the basis of the values for this variable.

10 Claims, 2 Drawing Sheets

METHOD OF IMAGING USING TOPOLOGIC ENERGY CALCULATION

BACKGROUND OF THE INVENTION

1. Field of the Invention

The present invention relates to an imaging method based on calculation of logical energy.

2. Discussion Of The Background

Imaging in two or three dimensions is traditionally used in industrial and medical applications, for example to make it possible to locate and characterize defects or obstacles in the interior of a liquid or solid medium by means of a nondestructive inspection method.

Under the English expression "pulse echo", there are already known ultrasonic imaging techniques using an ultrasonic transmitter/receiver probe capable of sending an incident pulsed wave to the propagation medium to be inspected and of receiving the field reflected or diffracted by the propagation medium in response to the incident wave, in order to transmit it for analysis.

Under the expression "topological gradient calculation method", there is already known an imaging method based on this technique, especially from the article entitled "*Flaw imaging with ultrasound: the time domain topological gradient method*", published in the periodical "*Review of Progress in Quantitative NonDestructive Evaluation Vol. 24A*, pp. 859-866, 2004", and from the article entitled "*Time domain topological gradient and time reversal analogy: an inverse method for ultrasonic target detection*", which appeared in the periodical "*Wave Motion vol. 42(1), pp. 31-52, 2005*". This method necessitates knowing the properties of a flawless reference medium, or in other words one that has identical composition, identical dimensions and identical physical structure as the part to be inspected but that with certainty contains no defects whatsoever, in contrast to the part to be inspected, which may possibly exhibit defects and/or inhomogeneities.

This method determines a "cost function", which evaluates the correlation between the data obtained for the reference medium and those measured on the medium to be inspected.

Starting from the reference medium, into which infinitesimal holes are introduced virtually and progressively, a "sensitivity analysis" (as it is known in English) is made of the cost function, in order to deduce therefrom modifications of the topology of the medium. The first stage of this analysis consists in solving a direct problem and what is known as an "adjunct" problem:

solving the direct problem consists in simulating the ultrasonic field $u_0$ generated by the propagation of an ultrasonic wave in a predetermined zone of a flawless reference part; and solving the adjunct problem consists in simulating the ultrasonic field $v_0$ generated in this predetermined zone of the reference part by the propagation of an ultrasonic wave corresponding to an incident wave $u_m-u_0$, where $u_m$ is the measured signal returned by the medium to be inspected in response to a known incident wave.

This analysis then consists in undertaking an asymptotic expansion of the "cost function" as a function of the topology of the medium. The first order term of this expansion gives the expression of a topological gradient as a function of the values of the $u_0$ and $v_0$ series. The most negative values of the gradient indicate where to insert the infinitesimal holes in order to cause the value of the "cost function" to become smaller and thus to make the modified topology tend toward that of the medium under inspection.

As used here, the term "hole" is a generic term that designates a zone exhibiting an abrupt contrast in elastic properties compared with the rest of the medium.

For reasons of simplification and visualization, the calculation of the topological gradient can be replaced in equivalent manner by the calculation of the corresponding topological energy. The image of the medium is then obtained by plotting the levels assumed by the topological energy, the defects being located at high values of this energy.

SUMMARY OF THE INVENTION

The objective of the invention is to provide an imaging method of the same type, but more precise and more reliable.

To this end it proposes a method for obtaining an image of a part to be inspected, characterized in that it includes the steps consisting in:

determining, by simulation, the ultrasonic field ($s_0$) generated by the propagation of an ultrasonic wave in a predetermined zone of a flawless reference part;

transmitting an ultrasonic incident wave toward a predetermined zone of the said part to be inspected corresponding to the said predetermined zone of the said reference part;

measuring the ultrasonic field ($u_m$) returned by the said part to be inspected in response to the said incident wave;

subtracting from the said ultrasonic field ($u_m$) returned by the said part to be inspected an ultrasonic field ($u_0$) obtained from a previous corresponding measurement on the said reference part;

calculating a variable related to the topological energy ($E_T$) in the reference part on the basis of the said ultrasonic field ($s_0$) determined by simulation and of the said field ($u_m-u_0$) obtained from the said measured fields ($u_0$, $u_m$) by subtraction; and determining the said image of the predetermined zone of the part to be inspected on the basis of the values assumed by the said variable.

The data obtained from the previous measurement ($u_0$) made on the reference part in the calculation of the subtractive signal are not data resulting from a simulation but are physical data obtained from real measurements. Thus the subtractive signal is obtained in this way by subtraction of two fields measured under identical conditions, and makes it possible to eliminate imprecisions related to the inherent differences between the results of simulation and the results of real measurement.

According to preferred characteristics:

the said topological energy ($E_T$) is selected as the said variable; and the step of calculating the topological energy includes the steps consisting in:

applying a time reversal to the said field ($u_m-u_0$) obtained from the said measured fields ($u_0$, $u_m$) by subtraction;

determining, by simulation, the ultrasonic field ($v_0$) generated in the said predetermined zone of the said reference part by the propagation of an ultrasonic wave corresponding to the said time-reversed subtractive field; and determining, for each position (x) of points in the said predetermined zone, the value of the topological energy ($E_T$) on the basis of the said first ($s_0$) and second ($v_0$) simulated ultrasonic fields, according to the formula $$E_T(x) = \sum_{i=1}^{N} \|s_0(x, t_i)\|^2 \|v_0(x, t_{N-i+1})\|^2.$$

Choosing the topological energy as variable makes it possible to simplify the calculations with which the image of the part to be inspected can be obtained.

the previous measurement on the said reference part is obtained by the steps consisting in:
transmitting the said ultrasonic incident wave toward the said predetermined zone of the said reference part; and
measuring the ultrasonic field ($u_0$) returned by the said reference part in response to the said incident wave.

The measurement of the ultrasonic field on the reference part is therefore achieved under conditions similar to those of the measurement performed on the part to be inspected, in order to minimize the risks of imprecision during the measurement.

a plane is selected as predetermined zone of the said reference part and of the said part to be inspected; or
a block is selected as predetermined zone of the said reference part and of the said part to be inspected; and possibly
the entire reference part is selected as predetermined zone of the said reference part, and the entire part to be inspected is selected as predetermined zone of the said part to be inspected.

The image of the part to be inspected can therefore be calculated in a single operation once all the measurements have been performed, or else it can be reconstituted from successive two-dimensional or three-dimensional images obtained respectively for planes or blocks of the part to be inspected.

an ultrasonic probe provided with at least one ultrasonic transducer is selected for transmission of the said ultrasonic incident wave; and possibly
an ultrasonic probe having an alignment of ultrasonic transducers in at least one direction is selected for transmission of the said ultrasonic incident wave; and possibly
an ultrasonic probe having two alignments of ultrasonic transducers in two distinct directions is selected for transmission of the said ultrasonic incident wave.

Depending on the number of ultrasonic transducers and on their distribution, it is therefore possible to have available a one-dimensional or two-dimensional scanning zone.

BRIEF DESCRIPTION OF THE DRAWINGS

The characteristics and advantages of the invention will become clear from the description hereinafter of a preferred example, given for illustrative but non-limitative purposes, with reference to the attached drawings, wherein.

DETAILED DESCRIPTION OF THE PREFERRED EMBODIMENTS

Figure 1:
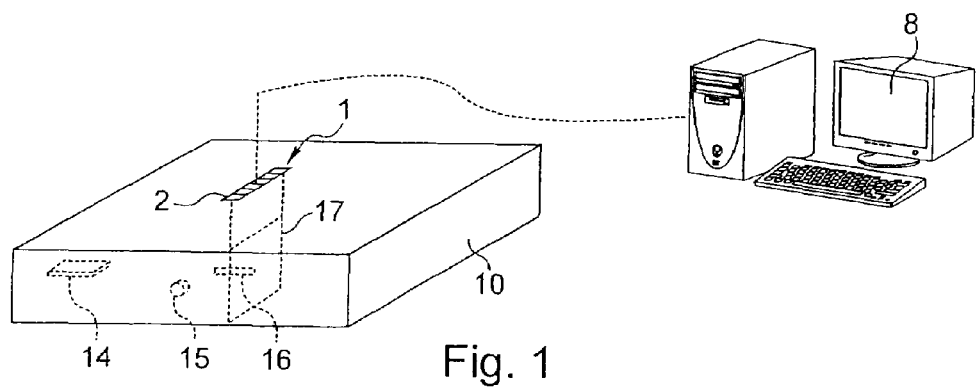
FIG. 1 is a schematic representation of an imaging device with which a method according to the invention can be used.

The device illustrated in FIG. 1 is provided with an ultrasonic probe 1 disposed above a part to be inspected and connected to a central calculator.

Ultrasonic probe 1 is a small bar composed of a plurality of aligned ultrasonic transducers 2 capable of transmitting and receiving ultrasonic signals according to the "pulse echo" technique.

Figure 2:
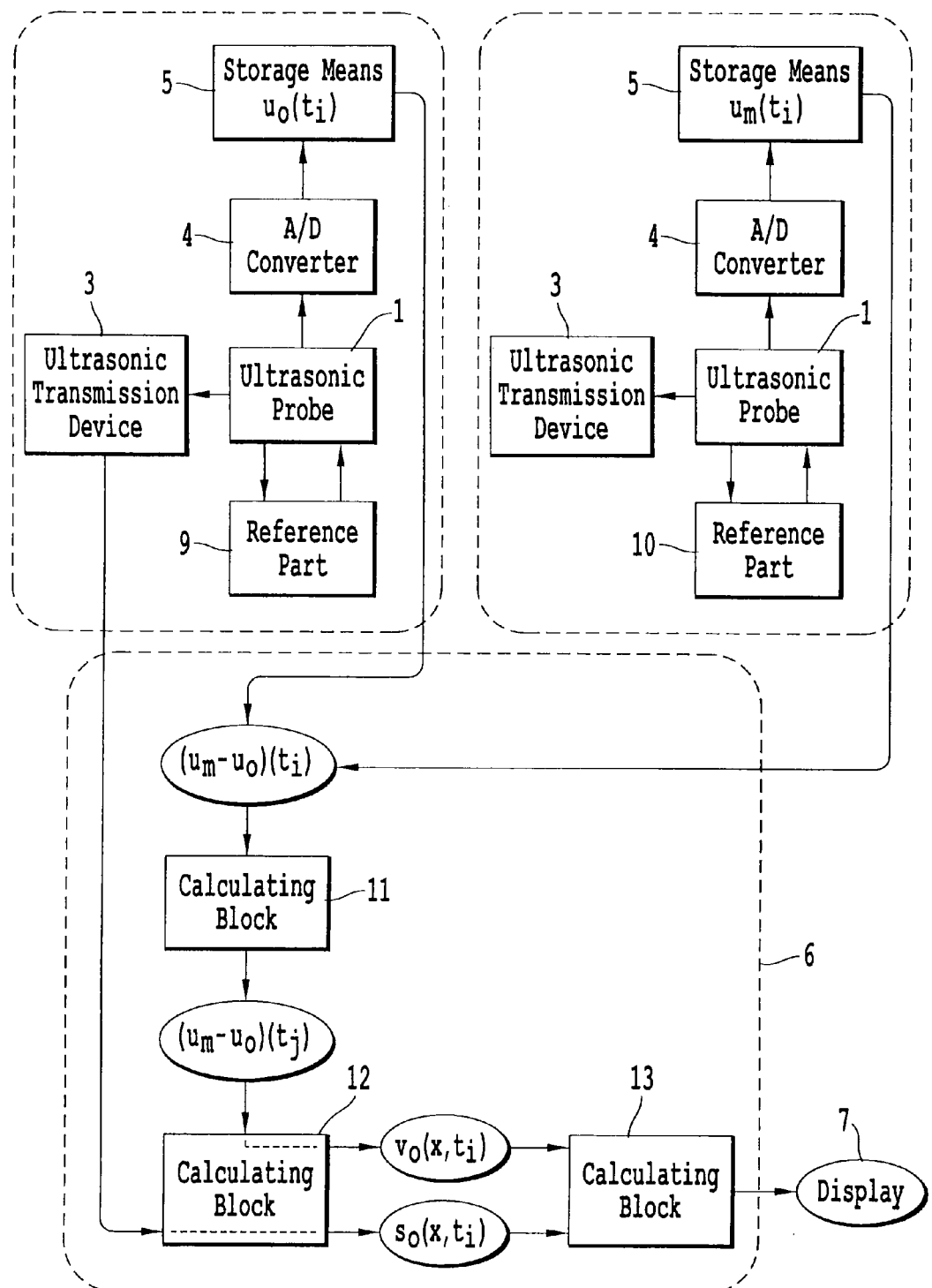
FIG. 2 is a diagram illustrating the different steps of this method.

The ultrasonic probe is connected to a signal generator 3 (FIG. 2).

As illustrated in FIG. 2, the central calculator is provided with analog-to-digital conversion means 4, means 5 for storage of data transmitted by probe 1, calculating means 6 and means 7 for displaying, on a screen 8 (FIG. 1), the image obtained as a function of the values assumed by the topological energy.

Calculating means 6 is provided in particular with calculating blocks 11, 12 and 13.

Ultrasonic probe 1 scans the surface of the part to obtain a succession of two-dimensional images corresponding to the images of section planes 17 of part 10 to be analyzed, which part may exhibit a plurality of defects 14, 15, 16 of variable geometry.

By means of FIG. 2 there will now be described the different steps of the method with which there can be calculated the topological energy and thus there can be obtained the image of a plane 17 of the part to be inspected for a given position of the probe above the said part.

A first ultrasonic measurement is performed on a reference part 9 known to be flawless, or in other words completely free of defects, having identical composition, identical dimensions and identical physical structure as part 10 to be inspected. For that purpose, probe 1 is disposed above the plane for which it is desired to obtain an image of the part, and an ultrasonic wave is transmitted by probe 1 toward reference part 9 by means of ultrasonic transmission device 3. The ultrasonic signal returned by the medium scanned is captured by this probe. This captured signal is transmitted to be digitized using analog-to-digital conversion means 4 and is stored in memory 5 in the form of a series of data $u_0(t_i)$ for all times $t_i = i\Delta t$, with i varying from 1 to N where N is the chosen number of time increments. These data correspond to the field values retransmitted by the reference part at the different instants $t_i$ for a given position of the probe above the reference part.

A first numerical calculation is then performed by simulation block 12 in order to simulate the propagation of the incident ultrasonic wave induced in the propagation medium of reference part 9. There is then obtained, at every position x of a point of the image of the medium (corresponding to one pixel of this image) and at every time $t_i = i\Delta t$, i=1 ... N, a simulated value of the ultrasonic field in the zone in which the simulation is performed in the form of a series of data $s_0(x, t_i)$.

This measurement and this simulation relative to the part known to be flawless can be performed once and for all prior to any measurement on the different but similar parts to be inspected, the measured data and the simulated data then being stored in memory prior to any measurement on the part to be inspected, for example in storage means 5.

A second ultrasonic measurement is performed by means of the same device on a part 10 to be inspected. Probe 1 is disposed above the plane for which it is desired to obtain an image of the part, in the present case a plane for which a measurement has been performed beforehand in the corresponding plane of the reference part.

As for the first measurement, a wave of identical characteristics is transmitted by probe 1 by means of signal generator 3 toward part 10, the sound signal returned by the medium scanned is captured by this probe, and the captured signal is transmitted to be digitized using analog-to-digital conversion means 4 and stored in the form of a series of data $u_m(t_i)$ in memory 5.

The field values $(u_0(t_i))$ measured on the reference part are subtracted by calculating means 6 from the values $(u_m(t_i))$ measured on the part to be inspected: the subtractive signal is therefore presented in the form of a series of data $u_m-u_0(t_i)$.

The subtractive signal is then subjected to time reversal in block 11. This operation comprises inverting the time scale: the subtractive signal $(u_m-u_0)(t_i)$ for i varying from 1 to N becomes the time-reversed subtractive signal $(u_m-u_0)(t_j)$ for j varying from N to 1.

A second numerical calculation is then performed by simulation block 12 in order to simulate the propagation of this time-reversed subtractive signal induced in the propagation medium of reference part 9 in the form of a series of data $v_0(x, t_i)$.

Block 13 can then calculate the topological energy at position x according to the formula:

$$E_T(x) = \sum_{i=1}^{N} \|s_0(x, t_i)\|^2 \|v_0(x, t_{N-i+1})\|^2$$

This calculation consists in summing, over the simulation time increments ($t_i$, for i varying from 1 to N), the pixel-by-pixel product of the squared norms $s_0^2$ and $v_0^2$ relative to the fields $s_0$ and $v_0$, read respectively in the order of advancing and retreating time.

$s_0$ corresponds to the direct field described in the articles mentioned hereinabove, while $v_0$ is the ultrasonic "adjunct" field in the time domain corresponding to the time reversal of the difference of the signals measured on the part to be inspected and on the reference part.

In this way the subtractive signal is obtained by subtraction of two fields measured under identical conditions, and makes it possible to eliminate imprecisions related to the inherent differences between the results of simulation and the results of real measurement.

The variables $s_0$ and $v_0$ used here correspond to the components of a displacement field coexisting dually in the material together with an associated constraint field.

If the data have been measured beforehand for all planes of the reference part, all measurements can be performed in one single operation for all planes of the part to be inspected. Probe 1 is then displaced to create the image of the next plane that is desired to be obtained.

For each image, the application of the topological energy algorithm described in the foregoing yields a map of topological energy levels. The user can then fix a threshold in order to retain only one limit level line for the purpose of representation of defects in the structure. The fixed threshold will be a function of the tolerance to defects which is considered to be acceptable.

Display means 7 control the display of the image of the part to be inspected on screen 8 as a function of the fixed threshold.

For each position of probe 1, the system therefore applies the topological energy algorithm described in the foregoing to create an image of the portion of the part to be inspected which has been subjected to the incident ultrasonic wave. These partial images can then be reassembled to form a three-dimensional global image of the internal structure of the inspected part.

It is also possible, in a single operation, to acquire and store in memory all the data for the entirety of the part to be inspected, and in this way to deduce directly therefrom a three-dimensional image by applying, in only one single operation, the topological energy algorithm to all of the data stored for the reference part and for the part to be inspected.

The measured ultrasonic field can also be zeroed at times corresponding to the entry and bottom echoes of the part, in order to improve the detection precision in the case in which it is desired to detect defects present in the body of the part and not situated in the proximity of its surfaces.

It is also possible to use the components of the constraint field or else a combination of the constraint field and of the displacement field for the calculations of $s_0(x, t_i)$ and $v_0(x, t_i)$.

In another embodiment of the device, the probe is composed only of a single ultrasonic transducer (mono-element probe). The probe is then displaced along two orthogonal directions in order to cover a surface of the part to be inspected.

In yet another embodiment, the transducer elements of the multi-element probe are disposed in two distinct spatial directions rather than being aligned in a single direction, so as to obtain, for a given position of the probe, by applying the topological energy algorithm, not the image of a plane but instead the image of a three-dimensional block, whose dimensions at its base correspond to the dimensions of the probe. The block images are then placed end-to-end in order to obtain the complete three-dimensional image of the part to be inspected.

In yet another embodiment, the image of the part to be inspected is determined by calculating a physical variable related to the topological energy, such as the topological gradient.

The present invention is not limited to the embodiments described and illustrated, but rather encompasses every variation of implementation thereof.

The invention claimed is:

1. A method for obtaining an image of a part to be inspected, said method comprising the steps of:
   determining, by simulation, a first simulated ultrasonic field ($s_0$) generated by propagation of an ultrasonic wave in a predetermined zone of a flawless reference part;
   transmitting an ultrasonic incident wave toward a predetermined zone of the said part to be inspected corresponding to the said predetermined zone of the said reference part;
   measuring an ultrasonic field ($u_m$) returned by the part to be inspected in response to said incident wave;
   obtaining a calculated field ($u_m-u_0$) by subtracting from the ultrasonic field ($u_m$) returned by the part to be inspected another ultrasonic field ($u_0$) obtained from a previous corresponding measurement on the said reference part;
   calculating a variable related to a topological energy ($E_T$) in the reference part based on said first simulated ultrasonic field ($s_0$) determined by simulation and on said calculated field ($u_m-u_0$); and
   determining the image of the predetermined zone of the part to be inspected based on values of said variable.

2. A method according to claim 1, wherein said topological energy ($E_T$) is selected as said variable.

3. A method according to claim 2, said calculating of the topological energy includes the steps of:
   applying a time reversal to the calculated field ($u_m-u_0$);
   determining, by simulation, a second simulated ultrasonic field ($v_0$) generated in said predetermined zone of the said reference part by propagation of an ultrasonic wave corresponding to the said time-reversed subtractive field; and determining, for each position (x) of points in said predetermined zone, a value of the topological energy ($E_T$) based on said first ($s_0$) and second ($v_0$) simulated ultrasonic fields, according to the formula $$E_T(x) = \sum_{i=1}^{N} \|s_0(x, t_i)\|^2 \|v_0(x, t_{N-i+1})\|^2.$$

4. A method according to claim 1, wherein the previous measurement on said reference part is obtained by the steps of:
  transmitting the ultrasonic incident wave toward the predetermined zone of the reference part; and
  measuring another ultrasonic field ($u_0$) returned by the reference part in response to the incident wave.

5. A method according to claim 1, further comprising selecting a plane as the predetermined zone of the reference part and of the part to be inspected.

6. A method according to claim 1, further comprising selecting a block as the predetermined zone of the reference part and of the part to be inspected.

7. A method according to claim 6, wherein the entire reference part is selected as the predetermined zone of the reference part, and the entire part to be inspected is selected as the predetermined zone of the part to be inspected.

8. A method according to claim 1, further comprising providing an ultrasonic probe with at least one ultrasonic transducer for transmitting said ultrasonic incident wave.

9. A method according to claim 8, wherein said ultrasonic probe has an alignment of ultrasonic transducers in at least one direction for transmitting said ultrasonic incident wave.

10. A method according to claim 9, wherein said ultrasonic probe has two alignments of ultrasonic transducers in two distinct directions for transmitting said ultrasonic incident wave.

* * * * *

UNITED STATES PATENT AND TRADEMARK OFFICE
CERTIFICATE OF CORRECTION

PATENT NO.       : 7,654,142 B2
APPLICATION NO.  : 11/526625
DATED            : February 2, 2010
INVENTOR(S)      : Dominguez et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 598 days.

Signed and Sealed this

Twenty-third Day of November, 2010

David J. Kappos
*Director of the United States Patent and Trademark Office*